(12) United States Patent
Weber et al.

(10) Patent No.: US 8,016,834 B2
(45) Date of Patent: Sep. 13, 2011

(54) PROCESS AND DEVICE FOR TREATING VERTEBRAL BODIES

(76) Inventors: Helmut Weber, Emmingen-Liptingen (DE); Nils Haberland, Frankfurt (DE)

( * ) Notice: Subject to any disclaimer, the term of this patent is extended or adjusted under 35 U.S.C. 154(b) by 442 days.

(21) Appl. No.: 11/195,898

(22) Filed: Aug. 3, 2005

(65) Prior Publication Data

US 2007/0032794 A1 Feb. 8, 2007

(51) Int. Cl.
*A61B 17/58* (2006.01)

(52) U.S. Cl. ............ 606/92; 606/279; 606/86 R; 606/79

(58) Field of Classification Search ............... 606/92, 606/93, 94, 95, 246, 279, 79, 86 R; 604/57–60, 604/118, 121, 181, 218; 623/17.11
See application file for complete search history.

(56) References Cited

U.S. PATENT DOCUMENTS

| | | | |
|---|---|---|---|
| 4,969,888 A | 11/1990 | Scholten et al. | |
| 5,108,404 A | 4/1992 | Scholten et al. | |
| 5,972,015 A | 10/1999 | Scribner et al. | |
| 6,019,765 A * | 2/2000 | Thornhill et al. | 606/94 |
| D439,980 S | 4/2001 | Reiley et al. | |
| 6,235,043 B1 | 5/2001 | Reiley et al. | |
| 6,241,734 B1 * | 6/2001 | Scribner et al. | 606/93 |
| 6,248,110 B1 * | 6/2001 | Reiley et al. | 606/93 |
| D449,691 S | 10/2001 | Reiley et al. | |
| 6,395,007 B1 * | 5/2002 | Bhatnagar et al. | 606/94 |
| 6,425,887 B1 * | 7/2002 | McGuckin et al. | 604/272 |
| 6,440,138 B1 * | 8/2002 | Reiley et al. | 606/79 |
| 6,575,919 B1 * | 6/2003 | Reiley et al. | 600/567 |
| 6,613,054 B2 | 9/2003 | Scribner et al. | |
| D482,787 S | 11/2003 | Reiss | |
| 6,641,587 B2 | 11/2003 | Scribner et al. | |
| 6,716,216 B1 | 4/2004 | Boucher et al. | |
| 6,719,773 B1 * | 4/2004 | Boucher et al. | 606/192 |
| 6,997,930 B1 | 2/2006 | Jaggi et al. | |

(Continued)

FOREIGN PATENT DOCUMENTS

EP 1 059 067 A1 12/2000

(Continued)

OTHER PUBLICATIONS dictionary.reference.com, acessed Feb. 9, 2009.*

*Primary Examiner* — Todd E Manahan
*Assistant Examiner* — Jan Christopher Merene
(74) *Attorney, Agent, or Firm* — Akerman Senterfitt; Peter A. Chiabotti

(57) ABSTRACT

The invention concerns a process for treating of vertebral body (70) with the following steps: introducing a trocar (10) and a trocar jacket (20) into the vertebral body (70), removing the trocar (10), introducing the same or a different biopsy and cement cannula (30) into the trocar jacket, extracting spongiosa (74) into the biopsy and cement cannula (30), removing the biopsy and cement cannula (30), filling a biopsy and cement cannula (30) with contact cement (60), introducing the biopsy and cement cannula (30) into the trocar jacket (20), and introducing the bone cement (60) into the vertebral body (70) by introduction of a plunger (40) into the biopsy and cement cannula (30). The invention further concerns a device for treatment of vertebral bodies with at least one biopsy and cement cannula, which are fillable with bone cement, and a plunger, which is introducible into the biopsy and cement cannula, in order to expel bone cement out of the biopsy and cement cannula.

11 Claims, 9 Drawing Sheets

U.S. PATENT DOCUMENTS

| | | |
|---|---|---|
| 7,226,481 B2 * | 6/2007 | Kuslich ............... 623/17.11 |
| 2001/0049531 A1 * | 12/2001 | Reiley et al. ............. 606/93 |
| 2002/0120240 A1 | 8/2002 | Bagga et al. |
| 2003/0036762 A1 * | 2/2003 | Kerr et al. ............... 606/93 |
| 2003/0036763 A1 | 2/2003 | Bhatnagar et al. |
| 2003/0105468 A1 | 6/2003 | Gorek |
| 2004/0010260 A1 * | 1/2004 | Scribner et al. ........... 606/93 |
| 2004/0030345 A1 * | 2/2004 | Aurin et al. .............. 606/92 |
| 2004/0073308 A1 * | 4/2004 | Kuslich et al. ......... 623/17.11 |
| 2004/0210231 A1 * | 10/2004 | Boucher et al. ........... 606/93 |
| 2005/0070912 A1 | 3/2005 | Voellmicke |
| 2006/0149280 A1 * | 7/2006 | Harvie et al. ............. 606/92 |
| 2006/0235425 A1 * | 10/2006 | Lin et al. ................ 606/92 |
| 2008/0200916 A1 * | 8/2008 | Murphy ................. 606/94 |

FOREIGN PATENT DOCUMENTS

| | | |
|---|---|---|
| EP | 1 459 689 A2 | 9/2004 |
| EP | 1 272 131 B1 | 3/2006 |
| WO | WO 0009024 | 2/2000 |
| WO | WO 0197721 | 12/2001 |
| WO | WO 02/02033 A1 | 1/2002 |
| WO | WO 0217801 | 3/2002 |

* cited by examiner

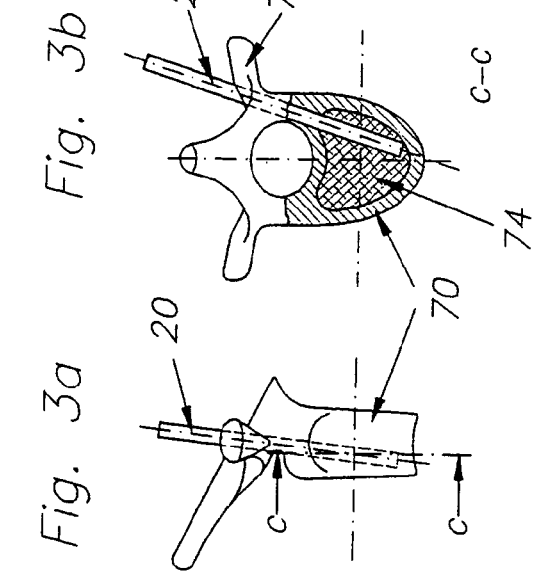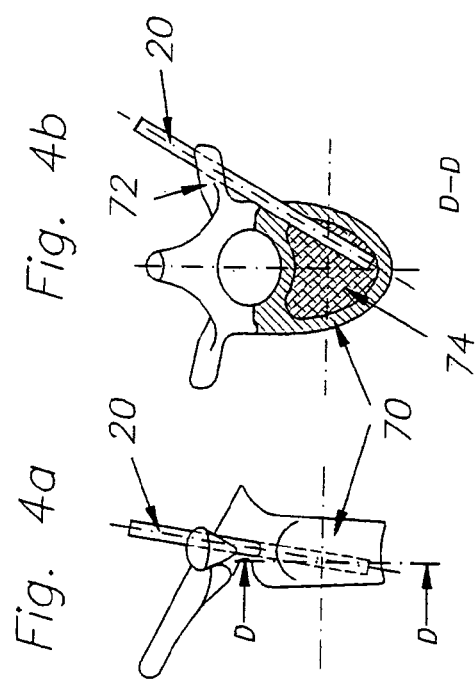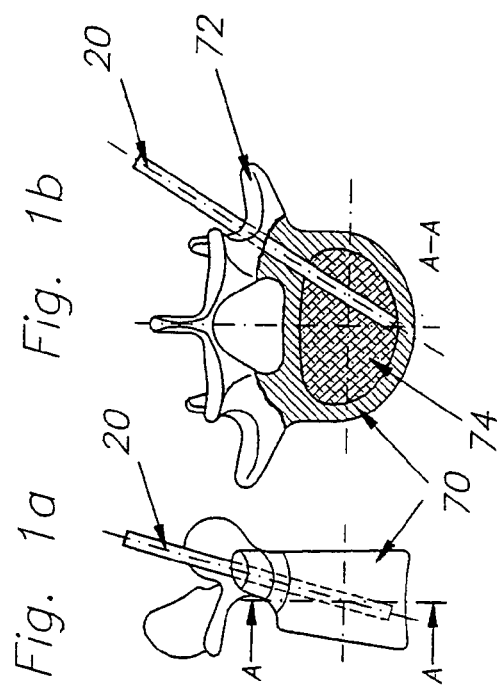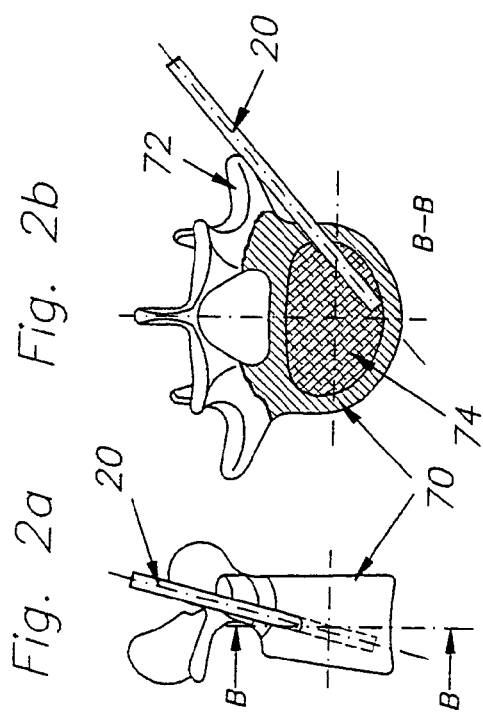

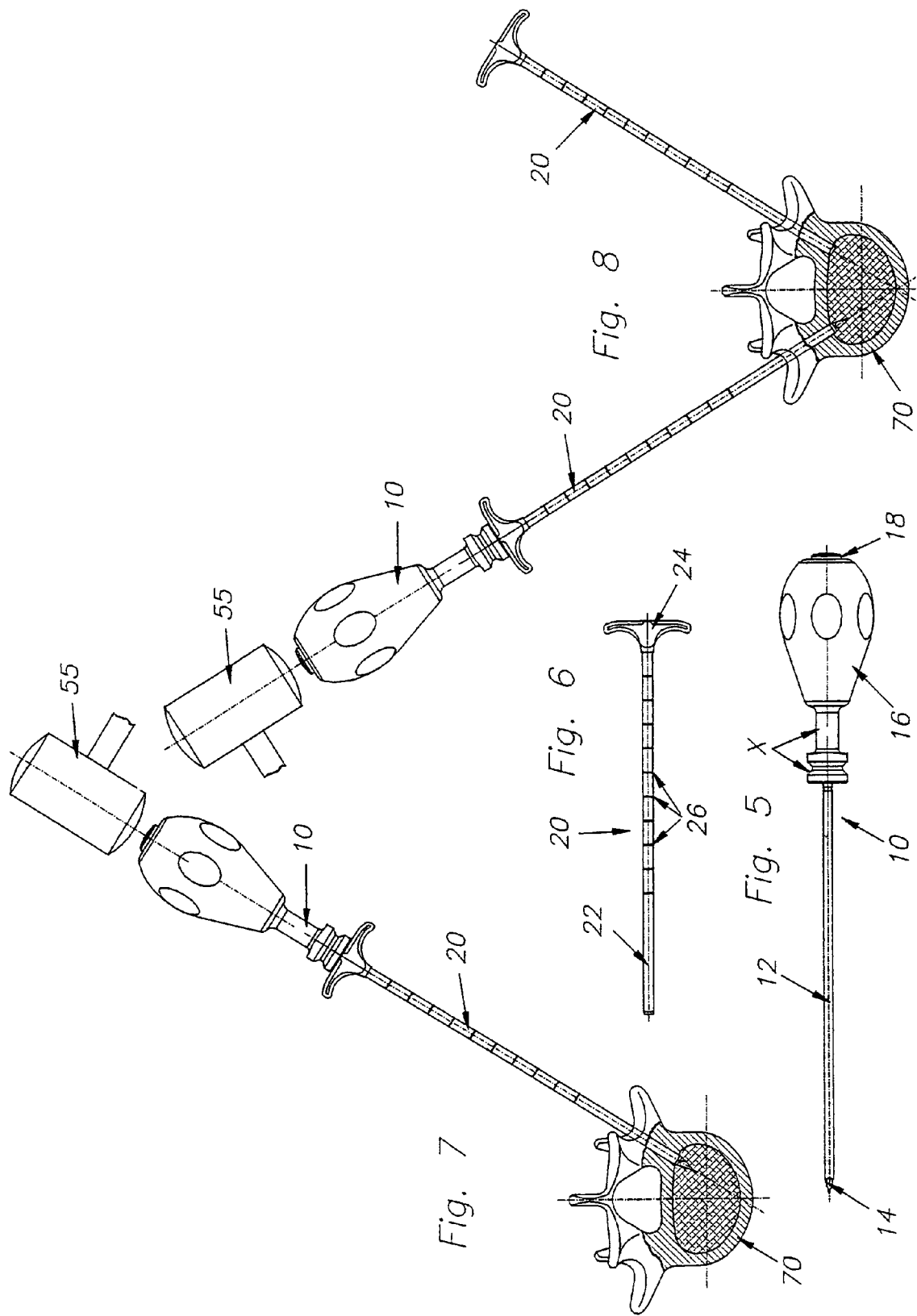

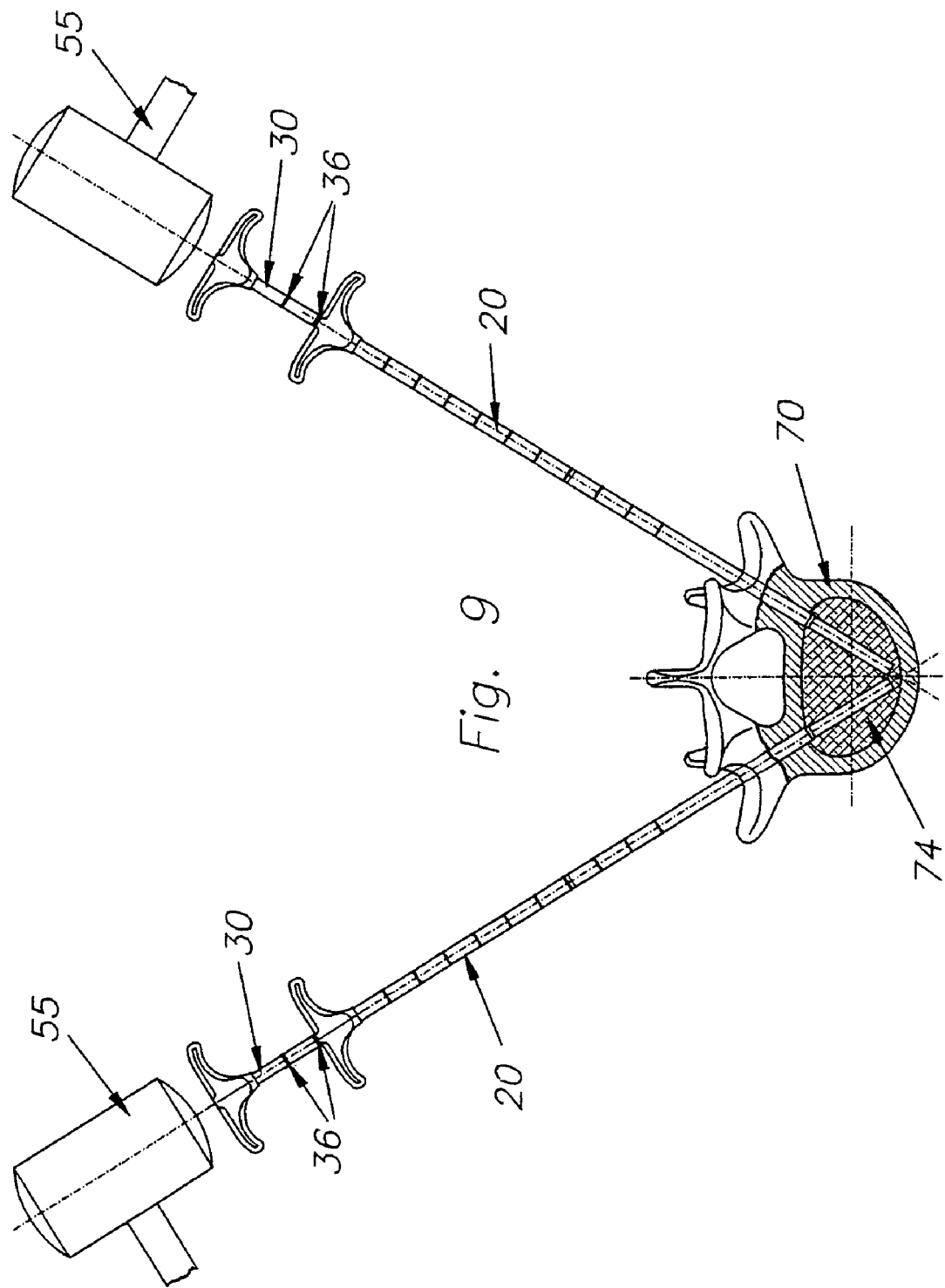

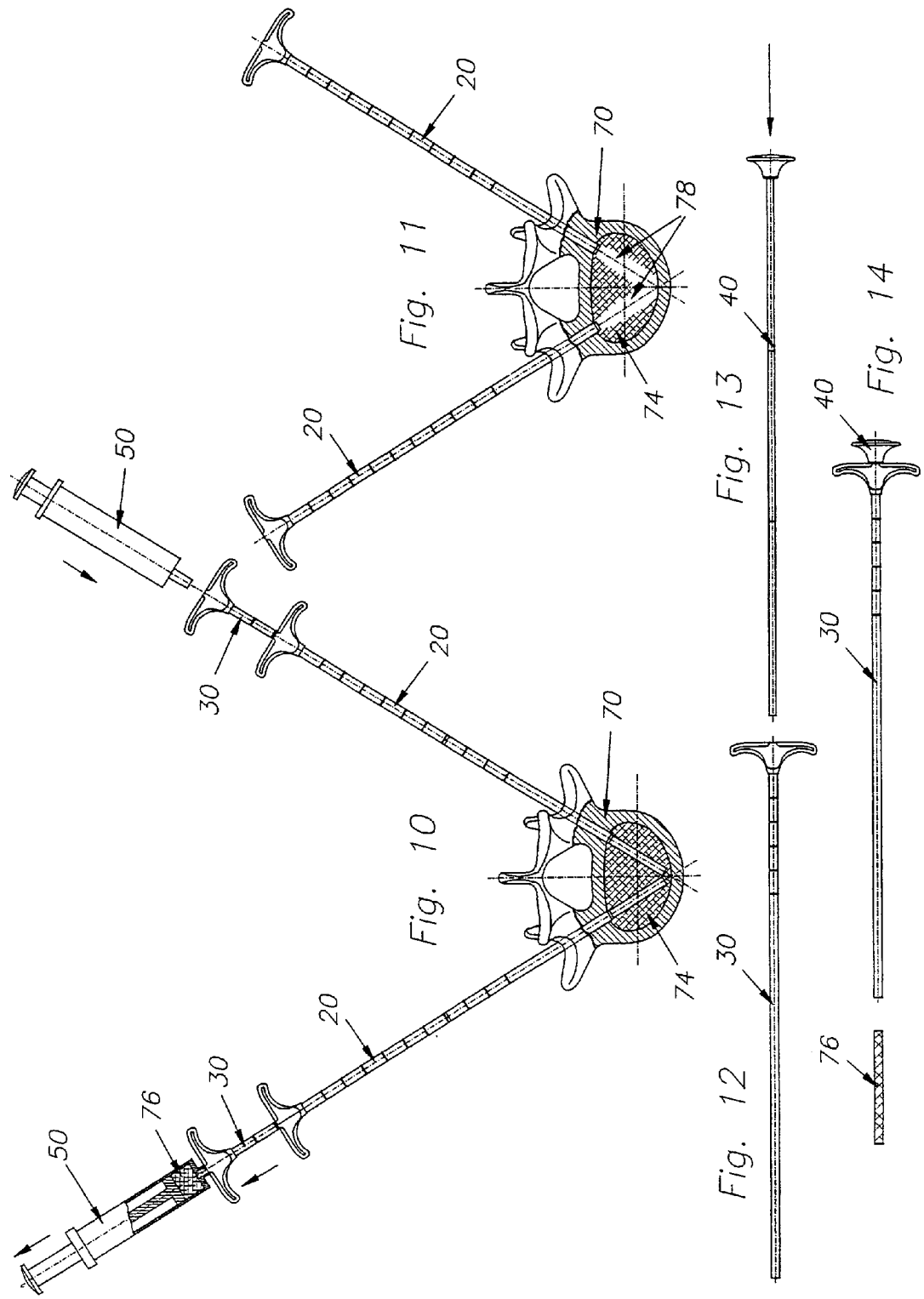

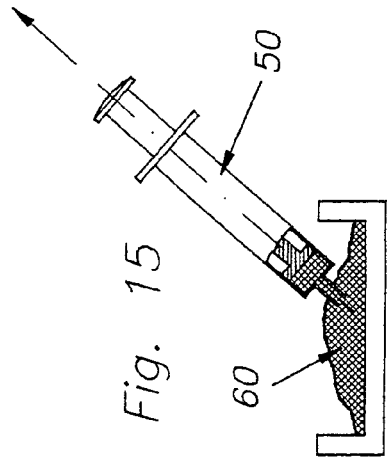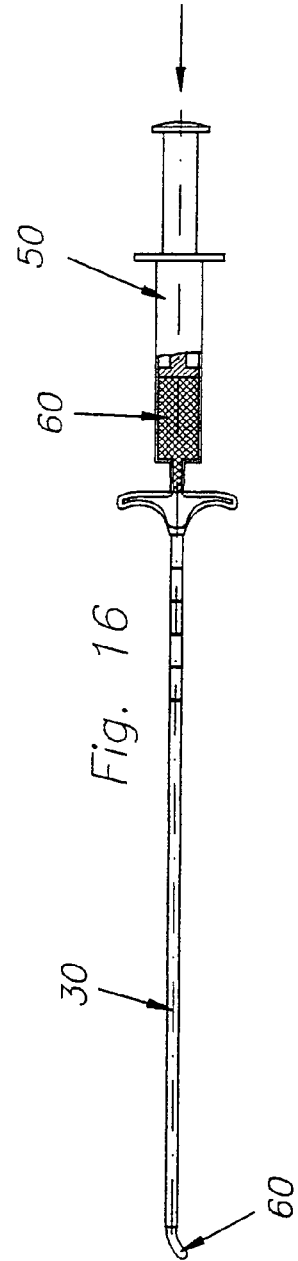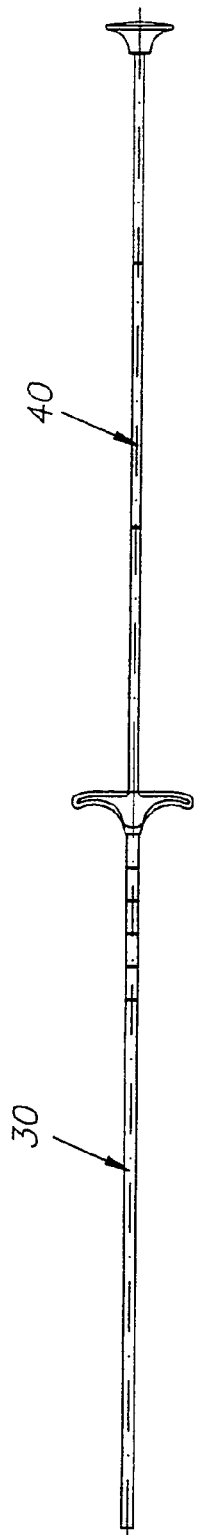

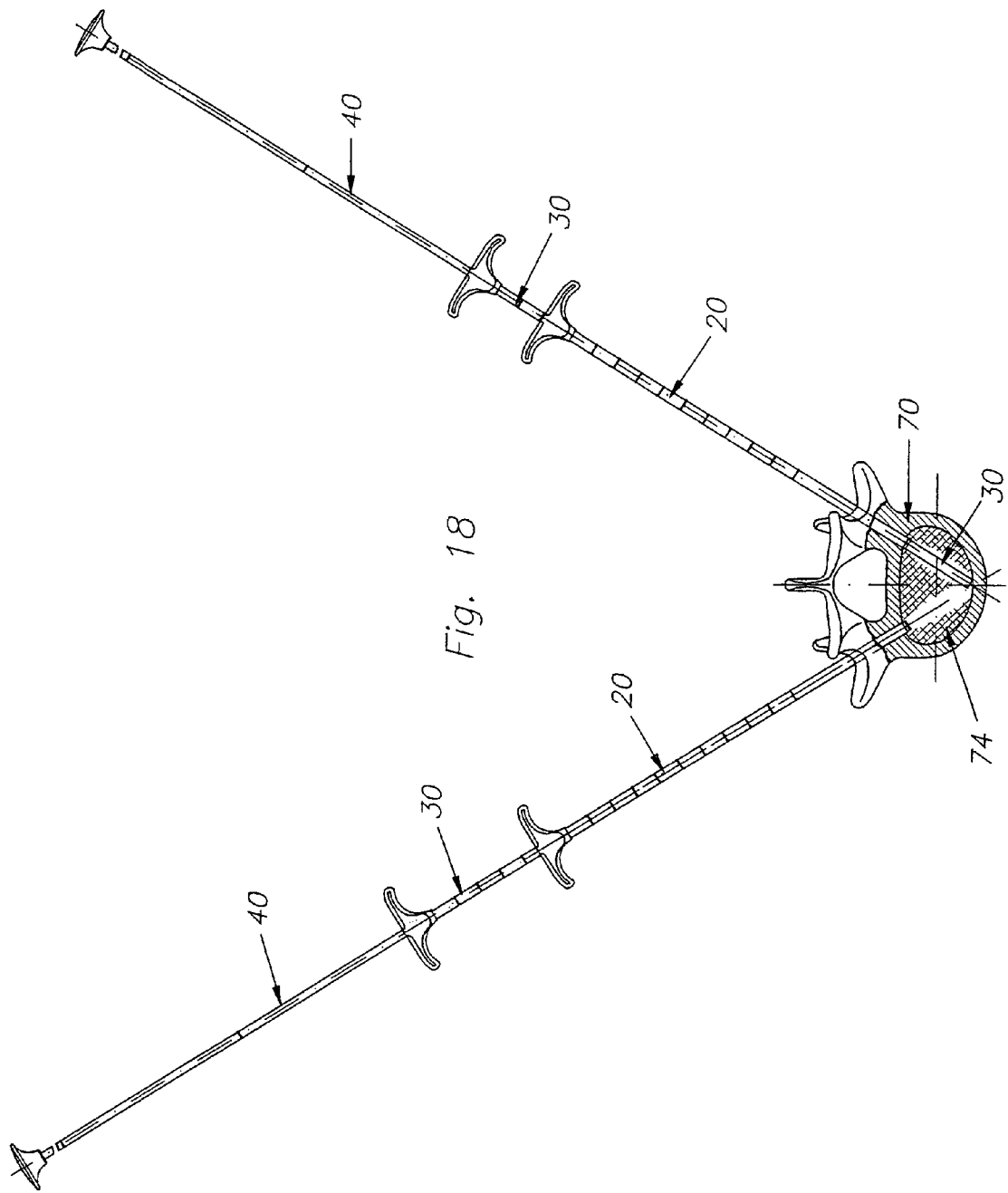

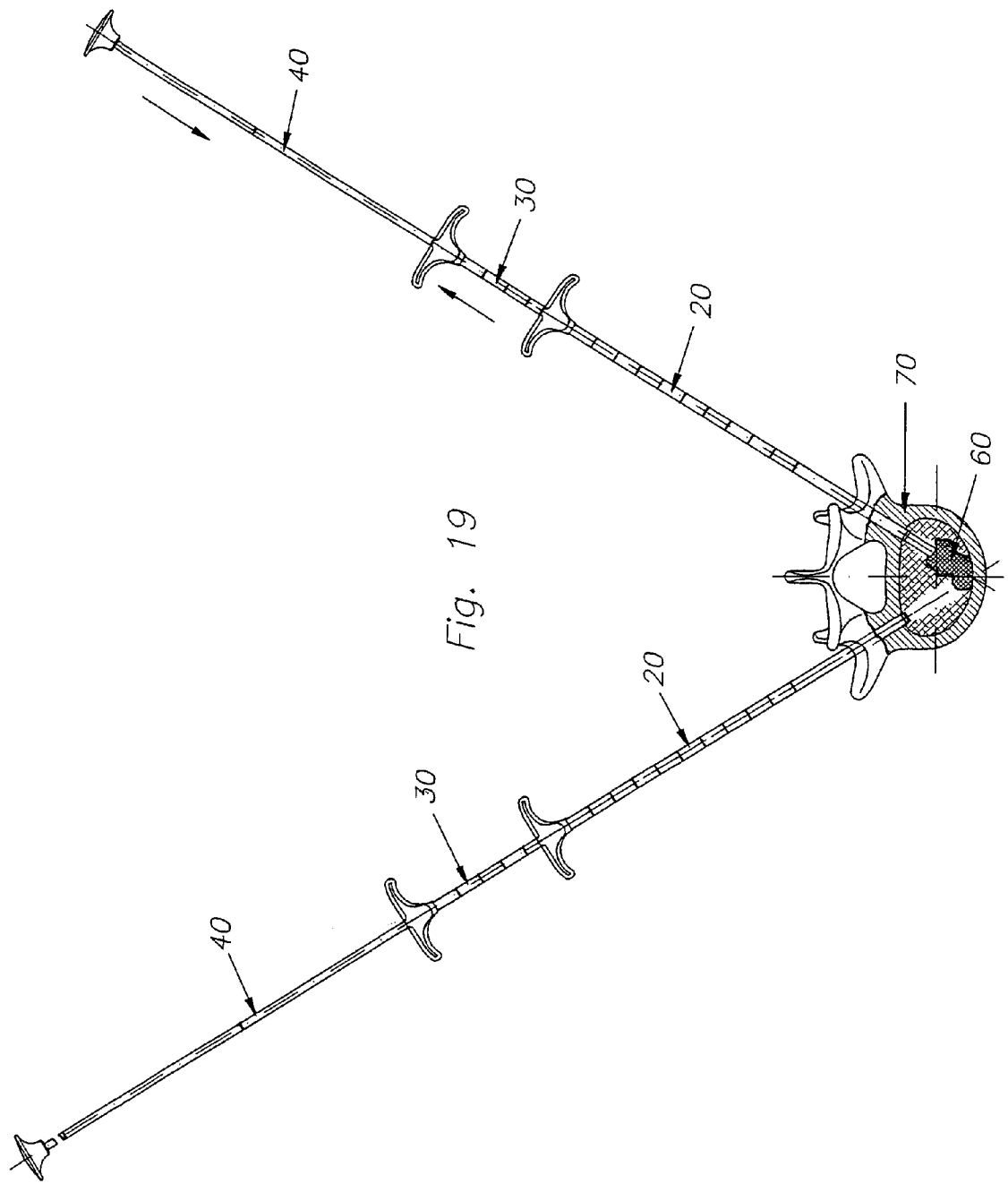

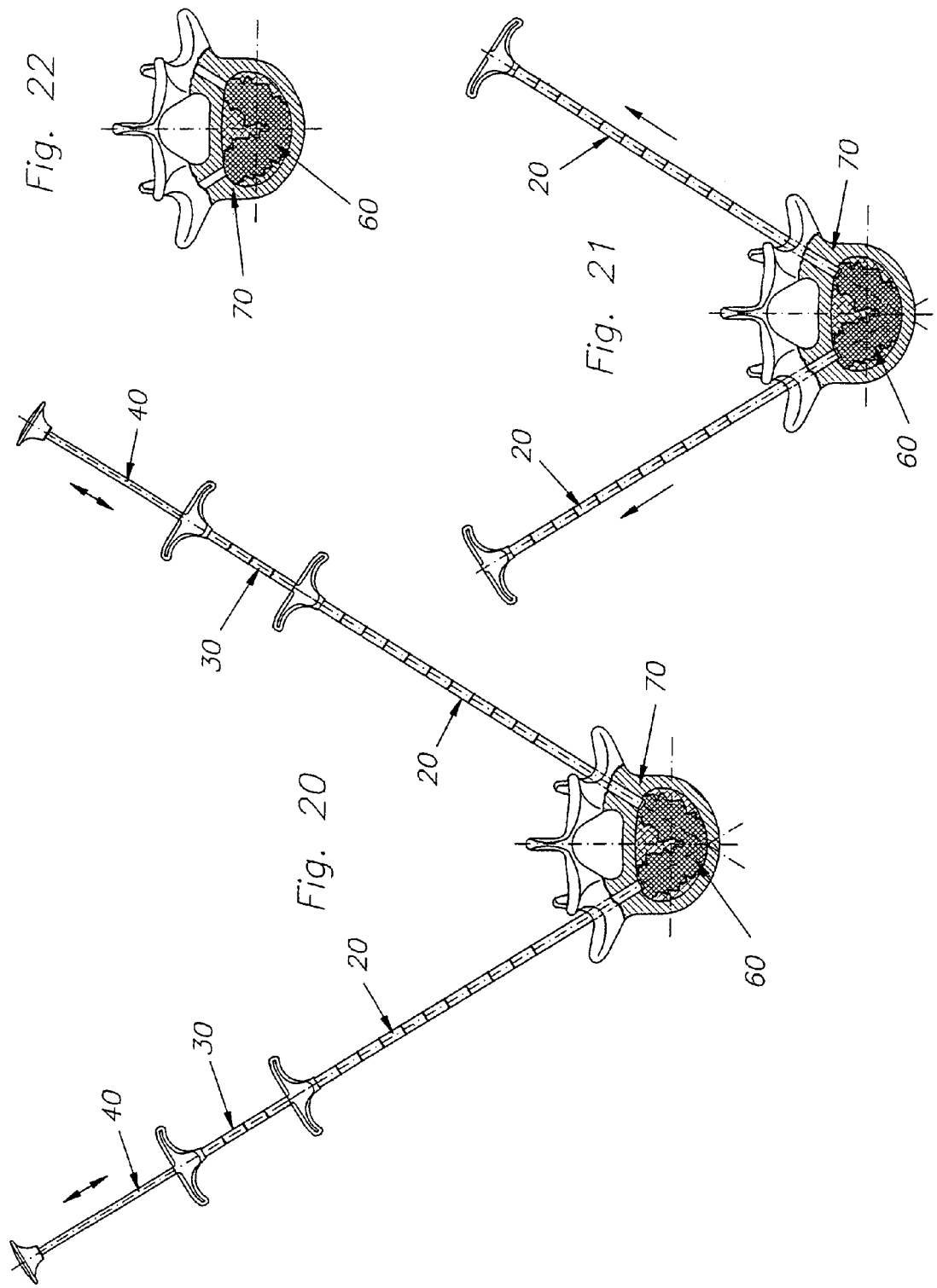

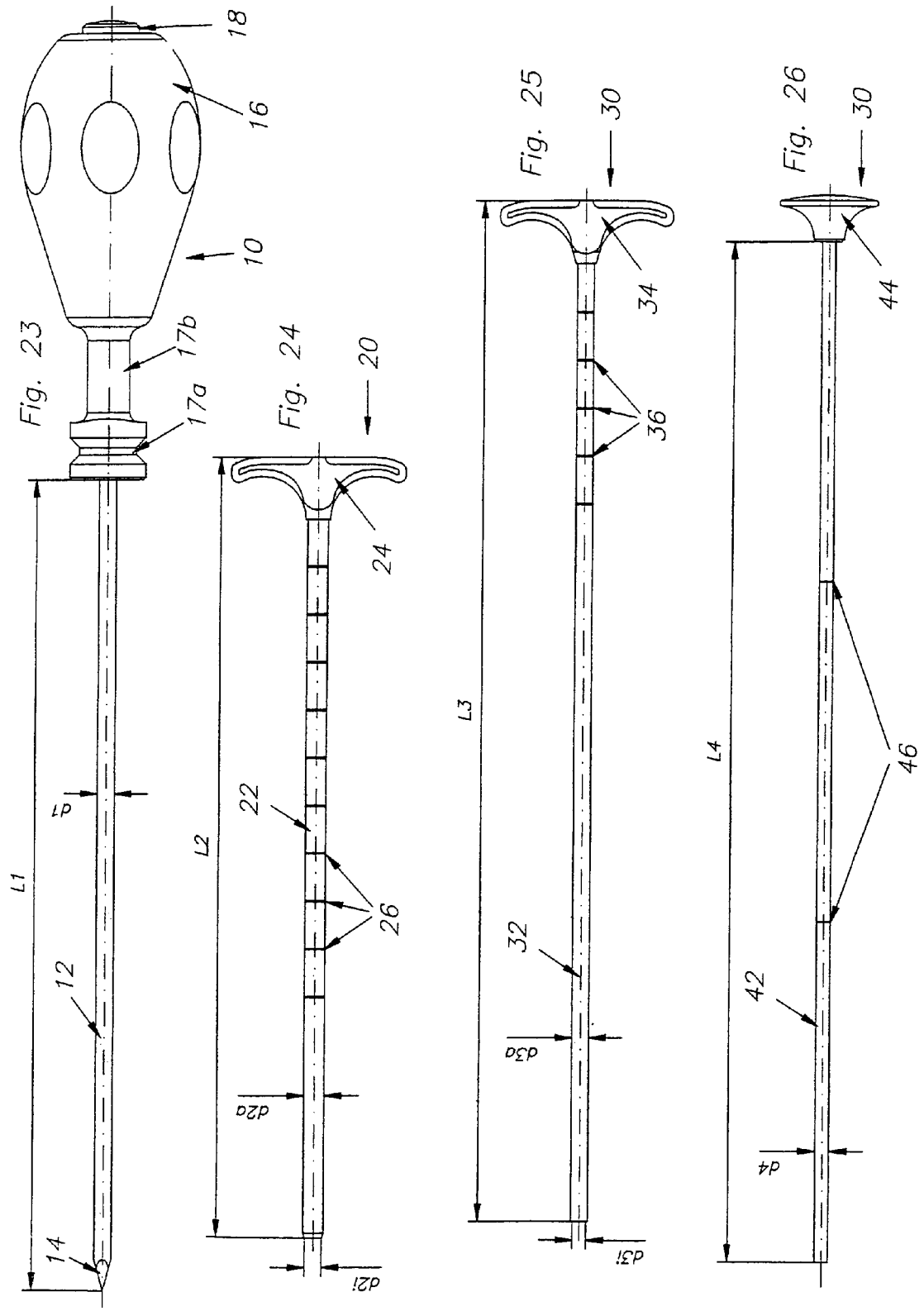

PROCESS AND DEVICE FOR TREATING VERTEBRAL BODIES

BACKGROUND OF THE INVENTION

1. Field of the Invention

The invention concerns a process and a device for treating vertebral bodies. Spinal diseases or diseases of the vertebral body such as osteoporotic vertebral body fractures, matastatic changed vertebral bodies or hemangioma of the spinal cord are treated using known minimally invasive fusing techniques, which stabilize the pathologically changed vertebrae and prevent the pain associated with the illness.

2. Related Art of the Invention

The conventional process of vertebroplasty includes the percutaneous dorsal introduction of liquid bone cement under pressure into the pathologically changed vertebrae, which, by appropriate positioning of the patient, is in certain cases repositioned. As a consequence of the use of liquid cement and the use of pressure there occurs however in this process routinely the egress of bone cement. If this occurs in the vertebral canal, then neurological consequences, even to the extent of paralysis, may result. Further, cement embolisms may occur in the lung in the case that the bone cement penetrates into the venous system.

SUMMARY OF THE INVENTION

The invention is thus concerned with the task of providing a process and a device with which an improved carrying out of the vertebroplasty process is made possible.

The task is solved by the inventive process for treatment of vertebral bodies according to claim 1 and the inventive device for carrying out the process according to Claim 10.

Advantageous embodiments and further developments of the invention are set forth in the dependent claims.

The inventive process for treatment of vertebral bodies includes the following steps: First a trocar jacket is introduced through the skin into the vertebral body with the assistance of a trocar. The trocar is subsequently removed. Subsequently a biopsy and cement cannula is introduced into the trocar jacket, spongiosa is drawn into the biopsy and cement cannula, and the biopsy and cement cannula is then removed from the trocar jacket. A biopsy and cement cannula, which is filled with bone cement, is subsequently introduced into the trocar jacket. Finally the bone cement is introduced into the vertebral body, in that a plunger is introduced into the biopsy and cement cannula, which presses the bone cement located in the biopsy and cement cannula out of the distal end of the biopsy and cement cannula.

The advantage of this process lies therein, that in contrast to the introduction of liquid bone cement with a hypodermic needle, in which the bone cement is pressed with pressure through a narrow needle, in the present case, by the targeted metered or dosed dispensing with use of the plunger, bone cement can be introduced into the vertebral body without having to force the bone cement with high pressure into the vertebral body, so that the danger of the emission of bone cement into the vertebral canal or the venous system is reduced. By the removal of at least parts of the spongiosa by means of the biopsy and cement cannula, a hollow space is produced in the vertebral body, into which the bone cement can subsequently be introduced.

The production of a hollow space, in which at least parts of the spongiosa is withdrawn from the vertebral body, has the advantage, that during the filling in of the bone cement no pressure would be exercised upon the vertebral body; further, diseased parts of the spongiosa can be completely removed and no longer remain in the vertebral body. In particular, it is achieved thereby, that since a hollow space is produced first, there results a good distribution of the bone cement in the area of the vertebral body, with good biomechanical anchoring.

In a particularly advantageous further development of the inventive process the bone cement is introduced in a pasty or semi-fluid condition into the vertebral body. It is precisely the processing of liquid bone cement under high pressure that presents itself as the main risk in the known process of vertebroplasty, since the liquid bone cement is particularly susceptible to being emitted into the vertebral canal or the veinous system. However, the use of a biopsy and cement cannula, from which the bone cement is dispensed by means of a plunger, makes possible the use of viscous bone cement. The viscous bone cement can ideally distribute itself in the vertebral body and there presents a very low risk of complication with respect to the emission of the cement out of the vertebral body.

Preferably, two biopsy and cement cannulas are introduced into the vertebral body via two trocar jackets. Thereby, a larger area of the inner space of the vertebral body is accessed, from which the spongiosa can be removed and bone cement introduced, whereby the vertebral body can be better stabilized. In order to reach the inner space of the vertebral body particularly effectively with two trocar jackets, two trocar jackets are preferably introduced symmetrically into the vertebral body.

Preferably the at least one trocar jacket is introduced into the vertebral body by a transpedicular approach, since this makes possible the most advantageous access to the vertebral body and to the inner space of the vertebral body. In particular, it becomes possible thereby to avoid damage of the nerve roots, which could possibly occur in the case of an extrapedicular access.

Preferably the plunger exhibits markings which correspond to the volume of the bone cement to be introduced into the vertebral body. If the plunger is introduced step for step in the biopsy and cement cannula, then it can be determined, on the basis of the markings provided on the outer circumference of the plunger, how much bone cement has already been expelled from the distal end of the biopsy and cement cannula and filled into the vertebral body.

Preferably the process is carried out at least section-wise using computer navigation and/or X-ray image control, in order to monitor the positioning of the trocar and the trocar jacket and/or the filling with bone cement and, as necessary, to make corrections. Preferably thus the entire procedure occurs under computer navigation and/or X-ray image control.

The inventive device for treatment of the vertebral body, in particular for use in the inventive process, includes at least one biopsy and cement cannula, which is fillable with bone cement, and a plunger, which is introducible into the biopsy and cement cannula. If the plunger is introduced step for step into the biopsy and cement cannula, then the bone cement is carefully extruded from the biopsy and cement cannula. This makes possible a dosed or metered extrusion of bone cement, with which in particular also viscous bone cement can be introduced into the inside of the vertebral body, which significantly reduces the risk of a cement leaving the target area and therewith associated damage in comparison to the introduction of liquid bone cement by means of a forced injection technique.

Preferably the plunger is in the form of a cylindrical rod with a knob on the proximal end, wherein the length of the cylindrical rod corresponds to the total volume of the biopsy and cement cannula. If the plunger is thus completely introduced into the biopsy and cement cannula, the distal end of the cylindrical rod comes into registry with the distal end of the biopsy and cement cannula. An introduction of the plunger beyond the length of the biopsy and cement cannula, which could lead to a damaging of the vertebral body, is therewith reliably prevented.

Preferably the outer diameter of the cylindrical rod of the plunger corresponds to the inner diameter of the biopsy and cement cannula. If the plunger is thus introduced into the biopsy and cement cannula, then the bone cement located therein and occupying this volume is completely displaced, thereby making possible a precise metering and dispensing of the amount of bone cement introduced into the inner space of the vertebral body. In particular, during the introduction of the plunger into the biopsy and cement cannula, no bone cement can exit at the proximal end of the biopsy and cement cannula. The metered dispensing is further made possible thereby, that the plunger exhibits markings on its outer circumference, which correspond to the volume of bone cement to be introduced into the vertebral body.

In an advantageous further development of the invention the biopsy and cement cannula also exhibits equidistant markings on its outer circumference. These serve to make it possible to determine how far the biopsy and cement cannula was inserted into the trocar jacket, in order to prevent that the biopsy and cement cannula is introduced too far into the inner space of the vertebral body, which could lead to a damaging of the vertebral body.

Preferably two biopsy and cement cannulas are employed, in order to improve the access to the inner space of the vertebral body and to make possible a more even filling of a greater area of the inner space of the vertebral body with bone cement.

Preferably the device includes a trocar and a trocar jacket. These are preferably coordinated in their dimensions to the biopsy and cement cannula, in order to make possible an optimal engagement.

Preferably the trocar is in the form of a cylindrical rod with a knob provided on the proximal end and a trocar tip provided on the distal end, wherein the length of the cylindrical rod without the trocar tip corresponds to the total length of the trocar jacket. The trocar can therewith be introduced into the trocar jacket to the extent that only the trocar tip projects beyond the trocar jacket. In this condition trocar and trocar jacket can be introduced into the vertebral body in a particularly simple manner.

In an advantageous embodiment of the invention the outer diameter of the cylindrical rod of the trocar corresponds to the inner diameter of the trocar jacket. Thereby a form-fitting seal between the cylindrical rod of the trocar and the trocar jacket is achieved, whereby the trocar, inclusive of the trocar jacket, allows itself to be introduced into the vertebral body in simple manner.

Preferably the trocar jacket exhibits markings on its outer circumference. Using these markings it can be read how far the trocar jacket has been introduced into the vertebral body.

Preferably the inner diameter of the trocar jacket corresponds to the outer diameter of the biopsy and cement cannula. Therewith also the biopsy and cement cannula can be introduced almost without play into the trocar jacket. Further, the outer dimensions of the trocar jacket are kept as small as possible, in order to make possible a gentle engagement with the vertebral body.

In a preferred further development of the invention the trocar is capable of computer navigation. For this it includes in particular connections for a navigation adapter. This enables a particularly safe introduction of the trocar into the vertebral body, whereby damage of the vertebral body can be substantially avoided.

Preferably the trocar includes on its knob a steel ring, preferably with connections for an X-ray target device. Otherwise the knob is comprised of a material, which is transparent for X-rays. Therewith, the introduction of the trocar inclusive of the trocar jacket can occur under X-ray image control, whereby in particular by the use of an X-ray target device a precise positioning of the trocar inclusive of the trocar jacket is made possible and damage to the vertebral body is avoided.

BRIEF DESCRIPTION OF THE DRAWINGS

An illustrative embodiment of the invention is described in the following in greater detail on the basis of figures. There is shown in:

FIG. 1a a side view through a lumbar vertebrae, in which a trocar jacket was introduced transpedicularly;

FIG. 1b a side view according to Line A-A in FIG. 1a;

FIG. 2a a side view through a lumbar vertebrae in which a trocar jacket was introduced extrapedicularly;

FIG. 2b a section along the Line B-B in FIG. 2a;

FIG. 3a a side view through a thoracic vertebrae, in which a trocar jacket was introduced transpedicularly;

FIG. 3b a section along Line C-C in FIG. 3a;

FIG. 4a a side view through a thoracic vertebrae, in which a trocar jacket was introduced transpedicularly;

FIG. 4b a section along the Line D-D in FIG. 4a;

FIG. 5 a view of a trocar;

FIG. 6 a view of a trocar jacket;

FIG. 7 a schematic representation of the process steps of the introduction of a trocar jacket in the vertebral body;

FIG. 8 a schematic representation of the process steps of the introduction of a trocar jacket in the vertebral body;

FIG. 9 a schematic representation of the process steps of the introduction of two biopsy and cement cannulas in a trocar jacket;

FIG. 10 a schematic representation of the process steps of the drawing in of spongiosa into the biopsy and cement cannulas;

FIG. 11 a schematic representation of the vertebral body, in which the spongiosa was partially removed;

FIG. 12 a view of the biopsy and cement cannula;

FIG. 13 a view of a plunger;

FIG. 14 a schematic representation of the process step of the removal of the biopsy sample from the biopsy and cement cannula;

FIG. 15 a schematic representation of the process step of the filling of the bone cement into a syringe;

FIG. 16 a schematic representation of the process step of the filling of the bone cement into the biopsy and cement cannula;

FIG. 17 a schematic representation of the biopsy and cement cannula with plunger seated;

FIG. 18 a schematic representation of the biopsy and cement cannula introduced into the trocar jacket with seated plunger;

FIG. 19 a schematic representation of the process step of the filling in of the bone cement in the vertebral body;

FIG. 20 a schematic representation of the vertebral body following the filling in process according to FIG. 19;

FIG. 21 a schematic representation of the vertebral body with removed biopsy and cement cannulas;

FIG. 22. a schematic representation of the vertebral body with introduced bone cement;

FIG. 23 a side view of a trocar according to one embodiment of the inventive device;

FIG. 24 a side view of a trocar jacket according to one illustrative embodiment of the inventive device;

FIG. 25 a side view of a biopsy and cement cannula according to an illustrative embodiment of the inventive device; and FIG. 26 a side view of the plunger according to one illustrative embodiment of the inventive device.

DETAILED DESCRIPTION OF THE INVENTION

First, an illustrative embodiment of the inventive device according to FIGS. 23 through 26 is described in greater detail, in order to be able to subsequently describe the use of the inventive device in the inventive process on the basis of FIGS. 1 through 22.

FIG. 23 shows a side view of a trocar 10 with a cylindrical rod 12 and a knob 16 provided on the proximal end of the rod 12 of a material which is transmissive for X-rays. The distal end of the rod 12 includes a trocar tip 14. The rod 12 exhibits, inclusive of the trocar tip 14, a length L1 of approximately 170 mm, wherein the trocar tip 14 has a length of approximately of 5 mm, and an outer diameter d1 of approximately 3.5 mm. At the transition between the cylindrical rod 12 and the knob 16 there are two connections 17a, 17b for a (not shown) navigation adapter. On the knob end there is a steel ring 18, which serves as X-ray target device.

The trocar 10 is introducible in a trocar jacket 20, which is shown in a side view in FIG. 24. The trocar jacket 20 includes a jacket 22 and a grip 24 provided on the proximal end of the jacket 22 of likewise X-ray transmissive material. The jacket 22 is defined by a cylindrical rod with an outer diameter d2a and an inner diameter d2i. Therein the inner hollow space of the jacket 22 continues through the grip 24, so that the trocar 10 can be introduced through the grip 24 into the jacket 22 of the trocar jacket 20. The outer diameter d2a of the jacket 22 is approximately 4.2 mm. The inner diameter d2i of the jacket 22 corresponds approximately to the outer diameter d1 of the rod 12 of the trocar 10, is however slightly larger, so that trocar 10 can be introduced, and is approximately 3.6 mm. The total length L2 of the trocar jacket 20 is 165 mm and corresponds therewith approximately to the length L1 of the cylindrical rod 12 of the trocar 10 without the length of the trocar tip 14. If the trocar 10 is introduced through the grip 24 into the trocar jacket 20 until the knob 16 bumps on the grip 24, then only the trocar tip 14 projects out of the jacket 22 from the distal end of the trocar jacket 20.

On the outer circumference of the trocar jacket 20 circumscribing markings 26 are provided. Preferably these markings are provided equidistant. In the present illustrative embodiment the distance of the markings 26 indicate approximately 10 mm. On these markings 26 it can be read, during the introduction of the trocar 10 inclusive of the trocar jacket 20 into the body of the patient, how far the trocar jacket 20 has already been introduced and in particular how far into the vertebral body.

FIG. 25 shows a side view of a biopsy and cement cannula 30 with a jacket 32 in the form of a cylindrical pipe and a grip 34 provided at the proximal end. The biopsy and cement cannula 30 exhibits a total length L3 of approximately 210 mm. The jacket 32 of the biopsy and cement cannula 30 exhibits an outer diameter d3a and an inner diameter d3i. Therein the inner hollow space continues through the grip 34. The outer diameter d3a of the biopsy and cement cannula 30 is approximately 3.5 mm and corresponds approximately to the inner diameter d2i of the trocar jacket 20, but is however slightly smaller in dimension, so that the biopsy and cement cannula 30 can be introduced into the trocar jacket 20. The inner diameter d3i of the biopsy and cement cannula 30 is approximately 3.1 mm.

The biopsy and cement cannula 30 exhibits circumscribing markings 36 beginning at the grip 34 located at the proximal end of the jacket 32, which markings are preferably provided equidistant. In the present illustrative embodiment the markings 36 are provided at a spacing of approximately 10 mm. On the basis of the markings 36 it can be read, how far the biopsy and cement cannula 30 has been introduced into the trocar jacket 20. The length L3 of the biopsy and cement cannula 30 is significantly greater, for example approximately a quarter of the length L3 greater, than the length L2 of the trocar jacket 20. This makes is possible that the distal end of the jacket 32 of the biopsy and cement cannula 30 projects also beyond the distal end of the jacket 22 of the trocar jacket 20, so that the biopsy and cement cannula 30 can be introduced further into the vertebral body than the trocar jacket 20. On the markings 36 it can thereby be precisely read, how far the distal end of the jacket 32 projects beyond the distal end of the jacket 22 of the trocar jacket 20 (distal end of the jacket 32 of the biopsy and cement cannula 30).

In FIG. 26 an illustrative embodiment of a plunger 40 is shown, which includes a cylindrical rod 42 of the length L4 and a knob 44 joining on the proximal end of the rod 42. The rod 42 exhibits an outer diameter d4, which is approximately 3 mm and therewith corresponds to approximately the inner diameter d3i of the biopsy and cement cannula 30, however is dimensioned slightly smaller, so that the plunger 40 and the biopsy and cement cannula 30 can be introduced.

The plunger 40 exhibits circumscribing markings 46 on the cylindrical rod 42, which are preferably provided equidistant spaced. In the present illustrative embodiment these are provided beginning at the distal end of the rod 42 and spaced approximately 70 mm apart. On the basis of the outer diameter of approximately 3 mm, such markings 46 with a spacing of 70 mm characterize a volume of approximately 0.5 cm$^3$. As the plunger 40 is introduced into a bone cement filled biopsy and cement cannula 30, the volume of the bone cement extruded from the distal end of the biopsy and cement cannula 30 can be read on the basis of the markings 46. If for example the plunger 40 is introduced by two markings 46 into the biopsy and cement cannula 30, there is expelled from the biopsy and cement cannula 30, which was completely filled with bone cement 60, a volume of approximately 1 cm$^3$ of bone cement 60 out of the distal end of the biopsy and cement cannula and into the vertebral body.

The length L4 of the rod 42 is approximately 210 mm and corresponds therewith approximately to the total length L3 of the biopsy and cement cannula 30. Therewith the plunger 40 can be completely pushed through the grip 34 into the biopsy and the cement cannula 30, until the knob 44 of the plunger 40 bumps on the grip 34 of the biopsy and cement cannula 30, and the distal end of the plunger 40 joins in this position sealingly with the distal end of the biopsy and cement cannula 30. Thereby it is ensured that the full volume of the bone cement is extruded out of the biopsy and cement cannula 30 and is emptied into the inside of the vertebral body.

In the following on the basis of FIGS. 1 through 22 the use of the illustrative embodiment of the inventive device with trocar 10, trocar jacket 20, biopsy and cement cannula 30 and plunger 40 is described in the inventive process.

In FIGS. 1a through 4b there is represented respectively a vertebral body 70 with pedicles 72 in the side view (FIGS. 1a, 2a, 3a and 4a) as well as a vertical section (FIGS. 1b, 2b, 3b and 4b). The vertebral body 70 shown in FIGS. 1a through 2b is a lumbar vertebra while in FIGS. 3a through 4b a thoracic vertebra is shown. FIGS. 1a through 4b show how the trocar jacket 20 is introduced into the vertebral body 70. In FIGS. 1a, 1b, 3a and 3b the transpedicular access is shown, and in FIGS. 2a, 2b, 4a and 4b the extrapedicular access is shown. Preferably in the following process the trocar jacket 20 is introduced transpedicularly into the vertebral body 70, since this simplifies the access to the vertebral interior. In particular in this way damage to the nerve roots, which could possibly occur in the case of extrapedicular access, can be avoided.

FIGS. 5 and 6 show the instruments employed in the first process step, namely the trocar 10 according to FIG. 23 as well as the trocar jacket 20 according to FIG. 24. The trocar 10 is slid into the trocar jacket 20, until the knob 16 of the trocar 10 bumps against the grip 24 of the trocar jacket 20, so that the trocar tip 14 projects from the distal end of the trocar jacket 20. The trocar 10 inclusive of the trocar jacket 20 is, as shown in FIG. 7, after exposing the access to the vertebral body 70, is introduced percutaneously dorsally and transpedicularly by careful hammering with a hammer 55 into the vertebral body 70, until the distal end of the trocar jacket 20 projects straight into the inner space of the vertebral body 70. This position can be determined on the basis of computer navigation and/or an X-ray imaging control or guidance, whereby supplementally an X-ray target device is employed. Preferably the entire process occurs under computer navigation and/or X-ray image control, in order to be able to control each process step. The computer navigation preferably occurs during the introduction of the trocar 10, in order to monitor the correct positioning of the trocar 10. In further progress of the process this can be dispensed with. From this point on preferably at least an X-ray image control is used during the complete process. If no data for computer navigation is available, then preferably two X-ray image controllers are employed.

As shown in FIG. 8, a second trocar jacket 20 is introduced likewise transpedicularly symmetrically to the first trocar jacket 20.

FIG. 9 shows how subsequently in each of the trocar jackets 20 respectively one biopsy and cement cannula 30 according to FIG. 25 is introduced. By the light tapping with a hammer 55 respectively right and left the biopsy and cement cannulas 30 are driven through the trocar jacket 20 up to the front edge of the vertebral body 70. On the markings 36 of the biopsy and cement cannula 30 it can be read how far the biopsy and cement cannula 30 was introduced into the trocar jacket 20. Since the length L3 of jacket 32 of the biopsy and cement cannula 30 is larger than the length L2 of the jacket 22 of the trocar jacket 20, the distal end of the biopsy and cement cannula 30 can be pushed out beyond the distal end of the trocar jacket 20. On the basis of the markings 36 it is monitored, that the distal end of the biopsy and cement cannula 30 projects only so far beyond the distal end of the trocar jacket 20 that it lies almost at the inner surface of the inner space of the vertebral body 70 lying opposite to the entry opening (see FIG. 9). The two biopsy and cement cannulas 30 transcend therewith essentially the inner space of the vertebral body 70.

FIG. 10 shows that a syringe 50 is seated upon the two grips 34 of the biopsy and cement cannulas 30, with which, by aspiration, spongiosa 74 from the inside of the vertebral body 70 is withdrawn through the biopsy and cement cannula 30. Therein simultaneously also the biopsy and cement cannulas 30 are pulled so far out of the trocar jacket 20, until approximately the distal end of the biopsy and cement cannulas 30 close the distal end of the trocar jacket 20, so that two essentially cylindrical hollow spaces 78 are produced in the inside of the vertebral body 70 (see FIG. 11). The hollow spaces 78 thereby have, in a lumbar vertebrae, a length of for example approximately 25 mm and a diameter of approximately 3 mm.

The production of the hollow spaces 78 simplifies and facilitates the introduction of the bone cement 60, which can distribute itself ideally in the hollow spaces, whereby the risk of a bone cement extrusion out of the vertebral body is reduced. Subsequently the two biopsy and cement cannulas 30 are removed from the trocar jacket 20 (See FIG. 11).

In FIGS. 12 through 14 it is shown that the biopsy and cement cannula 30 of the plunger 40 according to FIG. 26 is introduced, in order to push the obtained biopsy sample 76 out of the biopsy and cement cannula 30. The biopsy sample 76 can in certain cases be used for histological examination.

The term "bone cement" 60 is used in the following to refer to any material which is suited for stabilizing a bone, in particular a vertebral body. In particular, polymethyl-methacrylate (PMMA) or potassium phosphate cement can be employed as materials.

Subsequently the viscous bone cement 60 is filled into the biopsy and cement cannula 30. Thereby either the biopsy and cement cannula 30, with which the spongiosa 74 was withdrawn and which was subsequently cleaned, or an identically dimensioned or designed further biopsy and cement cannula 30 can be employed. In order to ensure that the biopsy and cement cannula 30 is completely filled, bone cement 60 is preferably filled in with the syringe 50 so long until this is emitted from the distal end of the biopsy and cement cannula 30 (See FIG. 16). This surplus or overspill of bone cement 50 is subsequently removed. Next, the plunger 40 is seated upon the proximal end of the biopsy and cement cannula 30 (See FIG. 17) and the biopsy and cement cannula 30 with seated plunger 40 is introduced into the trocar jacket 20 (See FIG. 18). Alternatively however also first the biopsy and cement cannula 30 can be introduced into the trocar jacket 20 and subsequently the plunger 40 can be seated upon the proximal end of the biopsy and cement cannula 30. The biopsy and cement cannula 30 are next introduced so far into the trocar jacket 20, that the distal end of the biopsy and cement cannula 30 projects beyond the distal end of the trocar jacket 20 and almost lies against the oppositely lying inner wall of the vertebral body (See FIG. 18).

In FIG. 19 the process step of the filling of the inner space of the vertebral body 70 with bone cement 60 is shown. The bone cement 60 is filled through the vertebral body 70, so that the plunger 40 is slowly advanced stepwise in the biopsy and cement cannula 30, while the biopsy and cement cannula 30 is stepwise extracted from the vertebral body 70. On the basis of the markings 36 on the biopsy and cement cannula 30 it can be monitored how far the biopsy and cement cannula 30 still projects into the inner space of the vertebral body 70, while on the basis of the markings 46 on the plunger 40 it can be checked how much bone cement 60 has already be filled into the vertebral body 70. The biopsy and cement cannula 30 is extracted from the trocar jacket 20 to the extent until the distal end of the biopsy and cement cannula 30 is in registry with or closes the distal end of the trocar jacket 20. This process step in particular is preferably monitored by X-ray image control, in order to be able to check the introduction of the bone cement 60 at each point and time and in certain cases to immediately terminate the filling in the case that bone cement 60 is emitted from the vertebral body 70.

In the same manner also via the second trocar jacket and the second biopsy and cement cannula 30 bone cement 60 is filled into the vertebral body 70 (See FIG. 20), while the first biopsy and cement cannula 30 remains in its position. If the necessary amount of the bone cement 60 is filled in, then the trocar jacket 20, the biopsy and cement cannulas 30 as well as the plunger 40 remain in the vertebral body 70 so long until the bone cement 60 is completely set. Subsequently, the plunger 40, the biopsy and cement cannulas 30 as well as the trocar jacket 20 are sequentially removed (See FIG. 21).

In FIG. 22 the final result of the operation is shown, which shows the vertebral body 70 with introduced bone cement 60. By the inventive process first a hollow space 78 is produced, in which viscous bone cement 60 from the biopsy and cement cannula 30 is pushed in with the assistance of the plunger 40 without pressure, whereby the risk of an emission of bone cement 60 out of the vertebral body 70 is significantly reduced.

REFERENCE LIST

10 Trocar
12 Rod
14 Trocar Tip
16 Knob
17a Connection for navigation adapter
17b Connection for navigation adapter
18 Steel ring
20 Trocar jacket
22 Jacket
24 Grip
26 Marking
30 Biopsy and cement cannula
32 Jacket
34 Grip
36 Marking
40 Plunger
42 Rod
44 Knob
46 Marking
50 Syringe
55 Hammer
60 Bone Cement
70 Vertebral body
72 Pedicle
74 Spongiosa
76 Biopsy sample
78 Hollow space
L1 Length (of the cylindrical rod of the trocar)
L2 Length (of the trocar jacket)
L3 Length (of the biopsy and cement cannula)
L4 Length (of the cylindrical rod of the plunger)
d1 Outer diameter (of the cylindrical rod of the trocar)
d2a Outer diameter (of the trocar jacket)
d2i Inner diameter (of the trocar jacket)
d3a Outer diameter (of the biopsy and cement cannula)
d3i Inner diameter (of the biopsy and cement cannula)
d4 Outer diameter (of the cylindrical rod of the plunger)

The invention claimed is:

1. A process for treating a vertebral body comprising the following steps:
   introducing two trocars and two trocar jackets into the vertebral body;
   removing the trocars, leaving the trocar jackets in place;
   extracting spongiosa of the vertebral body into a first biopsy cannula introduced into a first of the trocar jackets to form a first substantially cylindrical hollow space, and extracting spongiosa of the vertebral body into a second biopsy cannula introduced into a second of the trocar jackets to form a second substantially cylindrical hollow space, wherein the first and second substantially cylindrical hollow spaces are directly connected to each other only at their distal ends in the vertebral body;
   filling two cement cannulas with bone cement;
   introducing the respective filled cement cannulas into the respective trocar jackets such that a distal end of each respective cement cannula projects beyond a distal end of the respective trocar jacket into the first and second substantially cylindrical hollow spaces respectively, and almost lies against an oppositely lying inner wall of the vertebral body; and
   depositing the bone cement along both the first and second substantially cylindrical hollow spaces by stepwise advancement of a first plunger and a second plunger, respectively, into the respective cement cannulas, while the cement cannulas are stepwise extracted from the vertebral body for dosed or metered extrusion of the bone cement.

2. The process according to claim 1, wherein each of said first and second biopsy cannulas also form the cement cannulas.

3. The process according to claim 1, wherein the bone cement is filled into each cement cannula using a syringe.

4. The process according to claim 1, wherein the two biopsy cannulas are introduced symmetrically into the vertebral body.

5. The process according to claim 1, wherein the trocar jackets are introduced transpedicularly into the vertebral body.

6. The process according to claim 1, wherein additional spongiosa is not extracted beyond the spongiosa extracted to form the two substantially cylindrical hollow spaces.

7. The process according to claim 1, wherein the process occurs at least partially under computer navigation and/or X-ray image control.

8. The process according to claim 1, wherein the process occurs completely under computer navigation and/or X-ray image control.

9. The process according to claim 1, further comprising the step of positioning a distal end of the cement cannulas beyond a distal end of trocar jackets and into a hollow space of the vertebral body.

10. A process for treating a vertebral body with the following steps:
    extracting spongiosa of the vertebral body into two biopsy cannulas to form two substantially cylindrical hollow spaces directly connected at a distal end of the substantially cylindrical hollow spaces in the vertebral body;
    introducing at least two bone cement filled cement cannulas into the vertebral body such that a distal end of each cement cannula projects into each substantially cylindrical hollow space and almost lies against an oppositely lying inner wall of the vertebral body;
    depositing the bone cement along the substantially cylindrical hollow spaces by stepwise advancement of at least two plungers, respectively, into the respective cement cannulas, while each cement cannula is stepwise extracted from the vertebral body for dosed or metered extrusion of the bone cement;
    wherein additional spongiosa is not extracted beyond the spongiosa extracted to form the two substantially cylindrical hollow spaces.

11. The process according to claim 10, wherein the bone cement has a pasty or semi fluid consistency, whereby the bone cement is delivered in the substantially cylindrical hollow spaces and in hollow spaces in the vertebral body adjacent to the substantially cylindrical hollow spaces.

* * * * *